United States Patent [19]

Blade et al.

[11] Patent Number: 5,091,420

[45] Date of Patent: Feb. 25, 1992

[54] METHOD OF COMBATTING PESTS USING N-(CYCLO)ALKYL-5-SUBSTITUTED-2,4-THIOPENTADIENAMIDE COMPOUNDS

[75] Inventors: Robert J. Blade; Robert J. Peek, both of Berkhamsted, England

[73] Assignee: Burroughs Wellcome Co., Research Triangle Park, N.C.

[21] Appl. No.: 559,397

[22] Filed: Jul. 26, 1990

Related U.S. Application Data

[63] Continuation of Ser. No. 320,870, Mar. 7, 1989, which is a continuation of Ser. No. 8,974, Jan. 29, 1987, abandoned, which is a continuation-in-part of Ser. No. 877,104, Jun. 23, 1986, abandoned.

[51] Int. Cl.$^5$ .................. A01N 39/00; A01N 37/18; C07C 327/44
[52] U.S. Cl. .................. 514/599; 564/74; 564/78
[58] Field of Search .................. 564/74, 78; 514/599

[56] References Cited

FOREIGN PATENT DOCUMENTS

| | | |
|---|---|---|
| 0111105 | 6/1984 | European Pat. Off. |
| 209289 | 1/1987 | European Pat. Off. |
| 2533716 | 2/1976 | Fed. Rep. of Germany |
| 1514709 | 6/1978 | United Kingdom |

OTHER PUBLICATIONS

J. Meijer, et al., Recl. Trav. Chem., 92, 578, 1972, pp. 26–29, Chemistry of Acetylenic Ethers 104 Thermal Rearrangement of 1-Alkynyl 2-Alkynyl Sulfides in the Presence of Dialkylamines or dialkylphosphines, A new Type of Thio-Claisen.

J. Meijer, et al., Recueil. 92, 1973, pp. 1331–1334, Base-Catalyzed Cyclisatio of N.N-Dialkyl-2,4-Pentadienethioamides to 2-(Dialkylamino)Thiophenes.

Tamaru, Y. et al., J. Am. Chem. Soc., 100(16), pp. 5221–5223, 1978, 1,4–Addition Reaction of Organolithium and –Magnesium Compounds to a,β-Unsaturated Thioamides.

Chem. Abst., vol. 74, Jun. 1971, No. 23, pp. 401–402, Petrov et al., 1-History, Education and Documentation.

Tamaru, J. et al., Tet. Lett., 50(50), pp. 5797–5800, vol. 25, No. 50, (1984), Unusual Stereoselectivity in the Synthesis of 4–Oxa–δ–Valerothiolactones Structure Proof of β-Hydroxythioamide.

Petrov et al., "Chem. Abstracts", vol. 74, (1974) 12T738u.

Tamara et al., "Jour. Am. Chem. Soci.," (1978) pp. 5221–5223.

*Primary Examiner*—Mary C. Lee
*Assistant Examiner*—Michael G. Ambrose
*Attorney, Agent, or Firm*—Nixon & Vanderhye

[57] ABSTRACT

Pesticidal compositions for use against insects and acarines comprising a compound of Formula (I):

$$R^1-(CA=CA')_n C(=S)NR^2R^3 \qquad (I)$$

wherein $R^1$ is: $C_{1-14}$ alkyl optionally substituted by $C_{1-6}$ alkoxy, $C_{2-6}$ alkenyl, $C_{2-6}$ alkynyl, $C_{2-6}$ alkenyloxy, $C_{2-6}$ alkynyloxy, aryl, aryloxy or aryl $(C_{1-6})$ alkoxy; aryloxy or aryl $(C_{1-6})$ alkoxy; any of which groups may be substituted by halo, n is 1 or 2, each A and A' is independently hydrogen, halo, $C_{1-4}$ alkyl or halo $(C_{1-4})$ alkyl and $R^2$ and $R^3$ are independently hydrogen, $C_{1-6}$ alkyl or $C_{3-6}$ cycloalkyl, either of which may be substituted by one or more of halo, $C_{2-6}$ alkenyl, $C_{1-6}$ alkyl, $C_{3-6}$ cycloalkyl, $C_{3-6}$ cycloalkenyl, $C_{1-6}$ alkoxy, $C_{2-6}$ alkynyl or cyano, except that, when n is 1 and $R^2$ is alkyl and $R^3$ is hydrogen and A and A' are both hydrogen then $R^1$ is not substituted alkyl.

Most of the compounds of Formula (I) are novel.

4 Claims, No Drawings

METHOD OF COMBATTING PESTS USING N-(CYCLO)ALKYL-5-SUBSTITUTED-2,4-THIOPENTADIENAMIDE COMPOUNDS

CROSS REFERENCE TO RELATED APPLICATION

This is a continuation of copending application Ser. No. 07/320,870 filed on Mar. 7, 1989, now abandoned which is a continuation of Ser. No. 07/008,974 filed Jan. 29, 1987 which is a continuation-in part of copending application Ser. No. 877,104, filed 23 June 1986, the disclosure of which, to the extent necessary, is hereby incorporated herein by reference.

BACKGROUND OF THE INVENTION

This invention relates to pesticidal compounds and compositions.

EP-A-111 105 (The Wellcome Foundation Limited) discloses certain w-arylalkenamides as being acaricides or both acaricides and insecticides. It has now been found that certain unsaturated thioamides are also useful pesticides. GB 1 574 709 (Shell) discloses certain N-alkyl and cycloalkyl thioacrylamides as having fungicidal and, in some cases, insecticidal and/or acaricidal activity. W-Aryl compounds and compounds having two C=C groups conjugated to the thioamide group are not disclosed.

J. Meijer et al., in *Recl. Trav. Chim. Pay-Bas*, 93(1) 26–29 and ibid, 92(12):1331–4, and Y. Tamaru et al., in *J. Am. Chem. Soc.* 100(16):5221–3, disclose a wide range of aliphatic diene tertiary thioamides, but without ascribing any biological activity to them.

SUMMARY OF THE INVENTION

The present invention provides pesticidal compositions comprising a compound of Formula (I):

$$R^1-(CA=CA')_n C(=S)NR^2R^3 \qquad (I)$$

wherein $R^1$ is: $C_{1-14}$ alkyl optionally substituted by $C_{1-6}$ alkoxy, $C_{2-6}$ alkenyl, $C_{2-6}$ alkynyl, $C_{2-6}$ alkenyloxy, $C_{2-6}$ alkynyloxy, aryl, aryloxy or aryl ($C_{1-6}$) alkoxy; aryloxy or aryl ($C_{1-6}$) alkoxy; any of which groups may be substituted by halo,
n is 1 or 2,
each A and A' is independently hydrogen, halo, $C_{1-4}$ alkyl or halo ($C_{1-4}$) alkyl
and $R^2$ and $R^3$ are independently hydrogen, $C_{1-6}$ alkyl or $C_{3-6}$ cycloalkyl, either of which may be substituted by one or more of halo, $C_{2-6}$ alkenyl, $C_{1-6}$ alkyl, $C_{3-6}$ cycloalkyl, $C_{3-6}$ cycloalkenyl, $C_{1-6}$ alkoxy, $C_{2-6}$ alkynyl or cyano, except that, when n is 1 and $R^2$ is alkyl and $R^3$ is hydrogen and A and A' are both hydrogen then $R^1$ is not substituted alkyl.

A second aspect of the invention provides compounds of Formula (IA):

$$R^1-(CA=CA')_n C(=S)NR^2R^3 \qquad (IA)$$

wherein $R^1$ is: $C_{1-14}$ alkyl optionally substituted by $C_{1-6}$ alkoxy, $C_{2-6}$ alkenyl, $C_{2-6}$ alkynyl, $C_{2-6}$ alkenyloxy, $C_{2-6}$ alkynyloxy, aryl, aryloxy or aryl ($C_{1-6}$) alkoxy; aryloxy or aryl ($C_{1-6}$)alkoxy, n is 1 or 2,
each A and A' is independently hydrogen, halo or $C_{1-4}$ alkyl and $R^2$ and $R^3$ are independently hydrogen, $C_{1-6}$ alkyl or $C_{3-6}$ cycloalkyl, either of which may be substituted by one or more of halo, $C_{2-6}$ alkenyl, $C_{1-6}$ alkyl, $C_{3-6}$ cycloalkyl, $C_{1-6}$ alkoxy, $C_{2-6}$ alkynyl or cyano, except that;
(i) when n is 1 and $R^2$ is alkyl and $R^3$ is hydrogen and A and $A^1$ are both hydrogen then $R^1$ is not unsubstituted alkyl;
(ii) when $R^2$ is methyl and $R^3$ is hydrogen or methyl, then $R^1$ is not methyl or ethyl;
(iii) when neither of $R^2$ and $R^3$ is hydrogen and n is 2 and at least one of A and A'; is alkyl then $R^1$ is not methyl or ethyl;
(iv) where $R^2$ and $R^3$ are both methyl and n is 1 and A and A are both hydrogen, than $R^1$ is not isopropyl; and
(v) when $R^2$ and $R^3$ are both ethyl and n is 1 and A' is hydrogen, then $R^1$ is not methyl.

DETAILED DESCRIPTION OF THE PREFERRED EMBODIMENTS

Preferably, in Formula (I) and (IA) $R^1$ is one of the following groups:

  (A)

  (B)

in (A) or (B): AR is phenyl, furyl, thienyl, naphthyl, benzofuranyl or a polycyclic ring system having a partially or wholly saturated ring adjacent the unsaturated chain and fused to an aromatic ring, such as tetrahydronaphthyl, indanyl or indenyl, any of which Ar groups are optionally substituted by one or more of: halo; $C_{1-4}$ alkyl optionally substituted by $C_{1-4}$ alkoxy, halo or $C_{2-4}$ alkenyl (such as trifluoromethyl); $C_{1-4}$ alkoxy optionally substituted by halo (such as 2,3-methylenedioxy and 3,4-methylenedioxy); $C_{2-4}$ alkenyl optionally substituted by halo; acyl; cyano; and nitro the, or each, X is independently —O— or —CZ=CZ'— or —C≡C— where Z and Z' are independently hydrogen or halo
a is 0, 1 or 2 but is not 2 when X is oxygen
b is 1 to 10
c is 0, 1, 2 or 3
d is 0 to 6
Q is oxygen or —CH₂—
and e is 0 to 6.

It is preferred that one or more of the following features be present in Formula (A) and (B): Ar is optionally substituted phenyl, naphthyl, tetrahydronaphthyl, indanyl or benzofuranyl; any substituent on Ar is an electron withdrawing group such as halo or trifluoromethyl, particularly meta- $CF_3$; the, or each, X is CH=CH—; when a is zero, b is 1, 3 or 5 or 8; c is one; Q is —CH₂—; the sum of d and e is no more than 12, most preferably 3 to 7; and, when Q is —CH₂, the sum of d and e is preferably an odd number, most preferably 3 or 5.

In Formula (I) and (IA), n is preferably 2. A and A'[ are preferably both hydrogen. The configuration of the, or each, CA=CA' group is suitably E. $R^2$ is preferably hydrogen. $R^3$ is preferably a branched alkyl group such as isobutyl, 1,2-dimethylpropyl or 2,2-dimethylpropyl. It has been found that the acaricidal activity of compounds of Formula (I) is enhanced if there is an alkyl group attached to the nitrogen, for example $R^3$ is 1,2-dimethylpropyl.

Compounds of Formula (I) have been found to have activity against acarines and insects.

Compounds of Formula (I) may be prepared by one of the following routes:

(a) by reaction of a compound of Formula (II) with a compound of Formula (III):

$$R^1-(CA=CA')_g CHO \quad (II)$$

$$(Z^2)_2 P(O)_m CH_2(CA=CA^1)_h C(=S) NR^2R^3 \quad (III)$$

wherein $Z^2$ is alkyl, alkoxy (preferably ethoxy) or aryl (preferably phenyl), m is 0 or 1, and the sum of g and h is 0 or 1 (preferably g is 1 and h is 0);

(b) by reaction of the compound of Formula (IV) with phosphorus pentasulphide ($P_2S_5$), hydrogen sulphide, boron trisulphide, thiophosphoryl bromide or a compound of Formula (V):

$$R^1-(CA=CA')_n C(=O)NR^2R^3 \quad (IV)$$

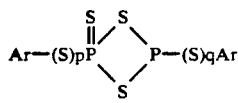

wherein p and q are each independently 0 or 1;

(c) when $R^2$ is hydrogen, by reaction of a compound of Formula (VI) with a compound of Formula (VII):

$$R^1-(CA=CA')_n-M \quad (VI)$$

$$SCNR^3 \quad (VII)$$

wherein M is a metal atom, preferably magnesium, lithium, aluminum or zirconium, or a function containing one of said metals;

(d) by elimination from a compound of Formula (VIII):

$$R^1-CA=CA'_{n-1}-(CHR^5-CHR^6)-C(=S)NR^2R^3 \quad (VIII)$$

wherein one of $R^5$ and $R^6$ is hydrogen and the other is $S(O)R^7$ where $R^7$ is aryl or alkyl, for example phenyl or $C_{1-4}$alkyl; followed by the optional conversion of one compound of Formula (I) to another, for example by hydrogenation of the triple bond when X is —C≡C— in group (A) above.

Route (a) is preferably performed in an anhydrous inert solvent, for example an ether such as tetrahydrofuran, optionally in the presence of a base and preferably in the absence of oxygen (e.g. under a nitrogen atmosphere) at a low temperature, for example −40° to 0° C.

Route (b) is preferably performed in an aromatic solvent such as toluene or xylene.

Route (c) is preferably performed in an anhydrous inert solvent such as an ether (e.g. tetrahydrofuran) in the absence of oxygen (e.g. under a nitrogen atmosphere).

Route (d) is preferably performed by refluxing in a solvent such as benzene or toluene.

The aldehyde of Formula (II) may be prepared by hydrolysis of a ketal ring or by oxidation of the corresponding alcohol, for example using pyridinium chlorochromate or oxalyl chloride/DMSO. The alcohol with an arylacetylene, arylalkadiyne or arylalkadiene compound, or by other methods disclosed in European Patent Publication No. 111 105. The alcohol may alternatively be formed by reduction of an ester obtained via a Wittig-type reaction with an aldehyde having one less unsaturated link than the aldehyde of Formula (II).

Alcohols containing an ether linkage may be prepared by standard methods, for example those taught in "Compendium of Organic Synthetic Methods", Harrison and Harrison, Wiley Interscience (New York, 1971).

Compounds of Formula (III) may be prepared from a compound of Formula (IX):

$$(Z^2)_2 P(O)-Alk, \quad (IX)$$

where Alk is lower alkyl, for example methyl, by reaction with a base and then an isothiocyanate $SCNR^3$.

Compounds of Formula (I) may be used to control arthroped pests such as insects and acarines.

The compounds of Formula (I) may be used for such purposes by application of the compounds themselves or in diluted form in known fashion as a dip, spray, lacquer, foam dust, powder, aqueous suspension, paste, gel, shampoo, grease, combustible solid, vapour emanator (e.g. coil, mat or the like), granule, aerosol, oil suspension, oil solutions, pressure-pack, impregnated article (such as a plastics ear tap or collar or a strip to treat the air of an enclosed space) or pour on formulation. Dip concentrates are not applied per se, but diluted with water and the animals immersed in a dipping bath containing the dip wash. Sprays may be applied by hand or by means of a spray race or arch. The animal, plant or surface may be saturated with the spray by means of high volume application or superficially coated with the spray by means of light or ultra low volume application. Aqueous suspensions may be applied to the animal in the same manner as sprays or dips. Dusts may be distributed over the animals by means of a powder applicator or incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) may be formulated either as formulations ready for use on the animals or as formulations requiring dilution prior to application, but both types of formulation comprise a compound of Formula (I) in intimate admixture with one or more carriers or diluents. The carriers may be liquid, solid or gaseous or comprise mixtures of such substances, and the compounds of Formula (I) may be present in a concentration of from 0.025 to 99% w/v depending upon whether the formulation requires further dilution.

Dusts, powder and granules comprise the compound of Formula (I) in intimate admixture with a powdered solid inert carrier for example suitable clays, kaolin, talc, mica, chalk, gypsum, vegetable carriers, starch and diatomaceous earths.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil), a wettable powder or a controlled release formulation, such as a microencapsulated formulation. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilizers and/or anti-oxidants.

Emulsifiable concentrates comprise emulsifying agents, and often or organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use. Microencapsulated formulations may be made by any known technique, for example coacervation or inter-facial polymerization.

Lacquers comprise a solution of the active ingredient in an organic solvent, together with a resin, and optionally a plasticizer.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. Aqueous solutions may also be formed from acid addition salts of a compound of the Formula (I). The suspensions or solutions may be applied per se or in a diluted form in known fashion. Electrostatic spraying techniques may be used with suitable formulations.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as a uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium which also contains a viscous oil to minimize spreading of the formulation on the surface of the animals. An avian or mammal host may also be protected against infestation of acarine ectoparasites by means of carrying a suitable moulded, shaped plastics article impregnated with a compound of Formula (I). Such articles include impregnated collars, tags, bands, sheets and strips suitable attached to appropriate parts of the body.

The concentration of the compound of Formula (I) to be applied to a locus (e.g. animal, grain, crop, soil, building etc.) will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% except for undiluted formulations such as pour-on formulations which in general will be deposited at a concentration in the range from 0.1 to 20.0% and preferably 0.1 to 10%. For public health usage, a deposited concentration of up to about 5% may be needed. The concentrate may contain up to 90% active ingredient.

Dusts, greases, pastes and aerosol formulations are usually applied in a random fashion as described above and concentrations of 0.001 to 20% w/v of a compound of Formula (I) in the applied formulation may be used.

Bait formulations for, example, cockroaches will include suitable attractants and/or foodstuffs. The compounds of the invention can be formulated specifically for use on grain or on the exposed surfaces of building, or for space spraying.

The compounds may be administered in an animal's feed to combat insect larvae infesting the animal's dung. Any suitable formulation, including microencapsulated material, may be used. The amount of the compound which is administered will vary according to the type and size of animal, and is chosen to provide a suitable concentration of the compounds in the animal's dung. Typically, 0.001 to 100 mg/kg body weight, preferably 0.1 to 10 mg/kg, are administered daily, to give concentrations of 0.001 to 1%, preferably 0.01 to 0.1% compound in the dung. The compound will usually be formulated as a concentrate or premix for mixing with a feed supplement, feed concentrate, roughage or the like. Alternatively, the compound may be added to the supply of drinking water. suitable animals include cattle, pigs, horses, sheep, goats and poultry.

Insect pests include members of the orders Coleoptera (e.g. *Anobium, Tribolium, Sitophilus, Diabrotica, Anthonomus, Hylotrupes* or *Anthrenus* spp.), Lepidoptera (e.g. *Ephestia, Plutella, Chilo, Heliothis, Spodoptera, Tinea* or *Tineola* spp.), Diptera (e.g. *Anopheles, Simulium, Musca, Aedes, Culex, Glossina, Stomoxys, Haematobia, Tabanus, Hydrotaea, Lucilia, Chrysomia, Callitroga, Dermatobia, Hypoderma. Lirimoyza,* and *Melaphaous* spp.), Phthiraptera (*Malophaqa* e.g. *Damalina* spp. and *Anoplura* e.g. *Linoqnathus* and *Haematipinus* spp.), Hemiptera (e.g. *Triatoma, Rhodnius, Aphis, Bemisia, Aleurodes, Nilopavata, Nephrotetix* or *Cimex* spp.), Orthoptera (e.g. *Schistocerca* or *Acheta* spp.), Dictyoptera (e.g. Blattella, Periplaneta or Blatta spp.), Hymemoptera (e.g. *Solenopsis* or *Monomorium* spp.), Isoptera (e.g. *Reticulitermes* spp.)] Siphonaptera (e.g. *Ctenocephalides* or *Pulex* spp.), Thysanura (e.g. *Lepisma* spp.), Dermaptera (e.g. *Forficula* spp.) and Psocoptera (e.g. *Peripsocus* spp.). Acarine pests include ticks, e.g. members of the genera Boophilus, Rhipicephalus, Amblyomma, Hyalomma, Ixodes, Haemaphysalis, Dermocentor and Anocentor, and mites and manges such as *Tetranychus, Pso-* roptes, Psoreroates, Chorioptes, Demodex, Dermatophaooides, Acarus, Tvrophaous and Glycyphaqus spp.

The compounds exhibit killing and/or knockdown activity against adult and/or larval arthropod pests.

Compounds of the invention may be combined with one or more other active ingredients (for example pyrethroids, carbamates and organophosphates) and/or with attractants and the like. Furthermore, it has been found that the activity of the compounds of the invention may be enhanced by the addition of a synergist or potentiator, for example: one of the oxidase inhibitor class of synergists, such as piperonyl butoxide or NIA 16388; a second compound of the invention; or a pyrethroid pesticidal compound. When an oxidase inhibitor synergist is present in a formula of the invention, the ratio of synergist to compound of Formula (I) will be in the range 25:1–1:25 e.g. about 10:1.

Stabilizers for preventing any chemical degradation which may occur with the compounds of the invention include, for example, antioxidants (such as tocopherols, butylhydroxyanisole and butylhydroxytoluene) and scavengers (such as epichlorhydrin).

It will be understood that what we will claim may comprise:
(a) compounds of Formula (IA);
(b) processes for the preparation of compounds of Formula (I);
(c) insecticidal and acaricidal compositions comprising a compound of Formula (I) in admixture with a carrier;
(d) processes for the preparation of such pesticidal compositions;
(e) methods for the control of insect or acarine pests comprising the application to the pest or its environment of a compound of Formula (I)
(f) synergised pesticidal compositions comprising a compound of Formula (I); and
(g) potentiating or non-potentiating mixtures of a compound of Formula (I) and another pesticidal compound;
(h) novel-intermediates of the preparation of compounds of Formula (I).

The following examples illustrate, in a non-limiting manner, preferred aspects of the invention.

EXAMPLE 1

N-isobutyl-2-(diethoxyphosphoryl)acetothioamide

N-Butyllithium (62.5 ml, 0.1 mol) was added at 70° C. to diethylmethane-phosphonate (15.2 g, 0.1 mol) in tetrahydrofuran (THF) (200 ml). After 30 minutes, isobutylisothiocyanate (5.8 g, 0.05 mol) in THF (50 ml) was added. The mixture was left overnight at room temperature then poured onto ice water and extracted with ether. The ether solution was washed with brine and dried and the solvents were removed to give an orange oil which was used after further purification.

TLC: Silica, ether, 1 spot $R_F$=0.17.

EXAMPLE 2

(2E,4E)-N-isobutyl-9-(3-trifluoromethyl benzyloxy)-nona-2,4-dienethioamide

N-isobutyl-2-(diethoxyphosphoryl) acetothioamide (0.45 g, 1.7 mmoles) in THF (5 ml) was added at −70° C. to lithium diisopropylamide (3.4 mmoles) in THF (15 ml). The temperature of the mixture was allowed to reach −20° C. and recooled to −40° C.

7-(3′-trifluoromethylbenzyloxy)-hept-2-en-al (0.4 g, 1.7 mmoles) in THF (5 ml) was added. The mixture was left overnight at room temperature and worked up in the standard manner. The crude material was purified by column chromatography (silica; 7:3 hexane: ether) to give the product as a yellow oil.

TLC Silica: 1:1 hexane: ether, 1 spot $R_F$ 0.29.

NMR Spectrum: 7.36 (5H), m, aromatic, H3; 6.16 (3H), m, H2, Hr, H5; 4.53 (2H), S, benzyloxy $CH_2$; 3.53 (2H), t, H9; 2.13 (2H), m, H6; 1.60 (4H), m, H7, H8; 3.53 (2H), d of d, 1.60 (1H), m, 0.96 (6H), d, isobutyl.

EXAMPLES 3–23

By analogous methods, the following compounds were made, the figure in brackets being the RF value for t.l.c., 1:1 ether: hexane or silica.

Example 3: (2E)-N-Isobutyl 6-phenylhexa-2-ene-thioamide (0.38

Example 4: (2E(4E)-N-Isobutyl 8-phenylocta-2,4-diene-thioamide (0.48)

Example 5: (2E)(4E)-N-dimethylpropyl 8-phenylocta-2,4-diene-thioamide (0.54)

Example 6: (2E,4E,10Z)-N-isobutyl-11-(3′-trifluoromethylphenyl)-undeca-2,4,10-trienethioamide (0.44)

Example 7: 2E,4E,10Z)-N-1,2-dimethylpropyl-11-(3′-trifluormethylphenyl(undeca-2,4,10-trienethiamide amide (0.33)

Example 8 (2E,4E)-N-(1,2-Dimethylpropyl)-12-(3,5-dichlorophenoxy)dodeca-2,4-dienethioamide (0.41)

Example 9: (2E,4E)-N-(Isobutyl-12-(3,5-dichloro phenoxy)dodeca-2,4-dienethioamide (0.36)

Example 10: (2E,4E)-N-Isobutyl-11-[3,5-bis(trifluoromethyl) benzyloxy)undeca-2,4-dienethioamide (0.45)

Example 11: (2E,4E)-N-(1,2-Dimethylpropyl)-11-[3,5-bis (triflurormethyl)benzyloxy]undeca-2,4-dienethioamide (0.43)

Example 12: (2E,4E)-N-Isobutyl-11-[(3,4-methylenedioxy) benzyloxy]undeca-2,4-dienethioamide (0.27)

Example 13: (2E,4E)-N-(1,2-Dimethylpropyl)-11-[(3,4-methylenedioxy)benzyloxy]undeca-2,4-dienethioamide (0.34)

Example 14: (2E,4E)-N-Isobutyl-6-phenylhexa-2,4-dienethioamide (0.32

Example 15: (2E,4E)-N-Isobutyl-13-phenyltrideca-2,4-dienethioamide (0.44)

Example 16: (2E,4E)-N-Isobutyl-9-[2(3-fluorophenoxy)ethoxy] nona-2,4-dienethioamide (0.19)

Example 17: (2E,4E)-N-(2,3-Dimethylpropyl)-9-[2-(3-fluorophenoxy)ethoxy]nona-2,4-dienethioamide (0.23)

Example 18: (2E,4E)-N-Isobutyl-8(3-trifluoromethylphenyl) octa-2,4-dienethioamide (0.32)

Example 19: (2E, 4E)-N-(1,2-Dimethylpropyl)-8-(3-trifluoromethylphenyl)octa-2,4-dienethioamide (0.37)

Example 20: (2E,4E)-N-Isoobutyl-9-(1-naphthyloxy)-nona-2,4-dienethioamide (0.28)

Example 21: (2E, 4E)-N-(1,2-Dimethylpropyl-9-(1-naphthyloxy)nona-2,4-dienethioamide (0.35)

Example 22: (2E,4E)-N-Isobutyl-11,11-difluoro-2,4,10-trienethioamide (0.40)

Example 23: (2E,4E)-N-Cyclohexyl-11-[3,5-bis(trifluoro-methyl)benzyloxy]undeca-2,4-dienethioamide (0.50)

BIOLOGICAL EXAMPLES

A. Activity against houseflies

The compounds are dissolved in Cellosolve, and applied topically to female *Musca domestica*. The strength of the solution is ⅓ the number of ug of compound applied; e.g. 3 μg would be applied as 0.3 ul of a 1% solution. Cotreatment with 6 μg of a synergist, piperonyl butoxide, was carried out in some instances. The results, as percentages of the flies dead after 48 hours are given in Table 1.

B. Activity against grain and flour pests 1.5 ml of a 0.2% w/v solution of the compound in acetone is pipetted onto 15g grain, left to dry, and infested with about 20 each of *Sitophilus granarius* and *Tribolium castaneum* adults % Mortality at 7 days is given in Table 1.

TABLE 1

| Compound of Example # | Amount (ug) | M. domestica % Kill alone | M. domestica % Kill +6 ugPB | Beetles pipette on kill at 200 ppm S.g. | Beetles pipette on kill at 200 ppm T.c. |
|---|---|---|---|---|---|
| 2 | 3 | 98 | 23 | 4 | 0 |
| 3 | 3 | 0 | 0 | 0 | 0 |
| 4 | 3 | 5 | 5 | 0 | 0 |
| 5 | 3 | — | 7.5 | | |
| 6 | 6 | — | 100 | 0 | 0 |
| 7 | 6 | 83 | 100 | 0 | 12 |
| 8 | 3 | — | 100 | 15 | — |
| 9 | 1.2 | 48 | — | | |
|   | 3 | — | 95 | 0 | 8 |
| 10 | 0.6 | 84 | 100 | 80 | — |
| 11 | 0.6 | 62.5 | 97.5 | | |
| 12 | 3 | — | 58 | 0 | 0 |
| 13 | 3 | 4.4 | 62.5 | 4 | 0 |
| 14 | 3 | — | 100 | 0 | 0 |
| 15 | 3 | — | 32 | 0 | 0 |
| 16 | 3 | — | 70 | 0 | 0 |
| 17 | 3 | 0 | 40 | 0 | 0 |
| 18 | 3 | — | 95 | 0 | 0 |
| 19 | 3 | 0 | 85 | 96 | 17 |
| 20 | 3 | 10.5 | — | | |
| 21 | 3 | 0 | — | | |
| 22 | 3 | 10 | 35 | | |
| 23 | 3 | 95 | 100 | | |

C. Activity against cattle ticks

The compounds were supplied as a 50 mg/litre solution in DMSO: Acetone (1:1). Administration of the compound was by means of a microapplicator which was preset to deliver 0.2 ul of solution. The compound in solution was injected into fully engorged female *Boophilus microplus*, susceptible strain, at a site just lateral to the mouthparts at the rate of 10 ug/tick. Reducing the concentration reduce the does delivered.

After injection the ticks were maintained at 24° C. and 85% RH for 14 days. At this time the ticks were examined for the presence of viable eggs which gave the per cent inhibition of reproduction (% IR). The number of dead ticks was also noted, and the results given in Table 2.

TABLE 2

| Example No. | % IR | % Kill |
|---|---|---|
| 4 | 30 | 30 |
| 7 | 20 | 0 |
| 10 | 10 | 0 |
| 12 | 10 | 10 |
| 17 | 20 | 20 |
| 18 | 90 | 90 |

TABLE 2-continued

| Example No. | % IR | % Kill |
|---|---|---|
| 19 | 40 | 10 |

D. Activity against blowfly larvae

*Lucilia cuprina* larvae were exposed to a deposit on paper equivalent to a 100 ppm solution of the test compound. The compounds of Examples Nos. 8, 9, 10, 11 and 12 effected 100% mortality after 3 days.

FORMULATIONS

1. Emulsifiable Concentrate

| | |
|---|---|
| Compound of Example 1 | 10.00 |
| Ethylan KEO | 20.00 |
| Xylene | 67.50 |
| Butylated Hydroxyanisole | 2.50 |
| | 100.00 |

2. Wettable Powder

| | |
|---|---|
| Compound of Example 1 | 25.0 |
| Attapulgite | 69.50 |
| Sodium isopropylbenzene sulphonate | 0.50 |
| Sodium Salt of condensed naphthalene sulphonic acid | 2.50 |
| Butylated hydroxytoluene | 2.50 |
| | 100.00 |

3. Dust

| | |
|---|---|
| Compound of Example 1 | 0.50 |
| Butylated Hydroxyanisole | 0.10 |
| Talc | 99.40 |
| | 100.00 |

4. Bait

| | |
|---|---|
| Compound of Example 1 | 40.25 |
| Icing Sugar | 59.65 |
| Butylated hydroxy toluene | 0.10 |
| | 100.00 |

5. Lacquer

| | |
|---|---|
| Compound of Example 1 | 2.5 |
| Resin | 5.0 |
| Butylated Hydroxy anisole | 0.5 |
| High aromatic white spirit | 92.0 |
| | 100.00 |

6. Aerosol

| | |
|---|---|
| Compound of Example 1 | 0.30 |
| Butylated Hydroxy anisole | 0.10 |
| 1,1,1-Trichloroethane | 4.00 |
| Odourless Kerosene | 15.60 |
| Arcton 11/12. 50:50 mix | 80.00 |
| | 100.00 |

7. Spray

| | |
|---|---|
| Compound of Example 1 | 0.1 |
| Butylated Hydroxy anisole | 0.1 |
| Xylene | 10.0 |
| Odourless Kerosene | 89.8 |
| | 100.00 |

8. Potentiated Spray

| | |
|---|---|
| Compound of Example 1 | 0.1 |
| Permethrin | 0.5 |
| Butylated Hydroxyanisole | 0.1 |
| Xylene | 10.1 |
| Odourless Kerosene | 89.2 |
| | 100.0 |

What is claimed is:

1. A method of combatting insects of acarids comprising applying to the insect or acarid or to the locus of either a compound of the formula

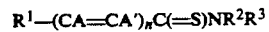

wherein $R^1$ is a $C_{1-14}$ alkyl group or a $C_{1-14}$ alkyl group substituted with either a phenyl, phenoxy, phenyl alkenyl or phenylalkoxy group, and the phenyl moiety may be substituted by either a halogen or trifluoromethyl group; A and A' are hydrogen atoms; n=2; and one of $R^2$ and $R^3$ is hydrogen and the other is a $C_{1-6}$ alkyl group or a $C_{3-6}$ cycloalkyl group.

2. The method according to claim 1, wherein the configuration of one or both (CA=CA') is E.

3. The method according to claim 1 or 2, wherein $R^2$ is hydrogen and $R^3$ is a branched alkyl group.

4. The method according to claim 1 or 2; wherein $R^3$ is isobutyl, 1,2-dimethylpropyl or 2,2-dimethylpropyl.

* * * * *